United States Patent [19]

Remy

[11] 4,031,223
[45] June 21, 1977

[54] TRIFLUOROMETHYLTHIO DERIVATIVES OF CYPROHEPTADINE

[75] Inventor: David C. Remy, North Wales, Pa.

[73] Assignee: Merck & Co., Inc., Rahway, N.J.

[22] Filed: Dec. 22, 1975

[21] Appl. No.: 642,864

[52] U.S. Cl. .......................... 424/267; 260/293.62
[51] Int. Cl.$^2$ ...................................... C07D 211/70
[58] Field of Search ............... 260/293.62; 424/267

[56] References Cited

UNITED STATES PATENTS 3,851,059  11/1974  Prugh ................................ 424/267

FOREIGN PATENTS OR APPLICATIONS 3,558M  9/1965  France

OTHER PUBLICATIONS

Ebnother et al., Helv. Chim. Acta 48(6), 1237–1249 (1965).

Yagupolskii et al., Synthesis, 721 (1975).

*Primary Examiner*—Cecilia M. S. Jaisle
*Attorney, Agent, or Firm*—William H. Nicholson; Harry E. Westlake, Jr.

[57] ABSTRACT

Cyproheptadine derivatives substituted with a trifluoromethylthio group in one of the benzo rings and certain derivatives thereof are potent antipsychotic agents, with a low propensity to induce extrapyramidal side effects experienced with most major tranquilizers, and platelet aggregation inhibitors useful as antithrombotic agents. The antipsychotic activity resides in the levorotatory enantiomer whereas both enantiomers are platelet aggregation inhibitors. The novel compounds are prepared by treatment of the corresponding iodo compound with trifluoromethylthiocopper formed from bis-(trifluoromethylthio)mercury and copper powder.

9 Claims, No Drawings

TRIFLUOROMETHYLTHIO DERIVATIVES OF CYPROHEPTADINE

BACKGROUND OF THE INVENTION

This invention is concerned with trifluoromethylthio derivatives of cyproheptadine which are potent antipsychotic agents, particularly the levorotatory enantiomer, and platelet aggregation inhibitors useful as antithrombotic agents.

Traditionally, in the dibenzocycloheptene series of compounds, those with a piperidinylidene group in the 5-position have been considered to be without notable antipsychotic action. Recently, however, 3-cyanocyproheptadine, and particularly the levorotatory isomer was found to have antipsychotic activity and the dextrorotatory isomer was found to have anticholinergic activity.

Furthermore, racemic 3-trifluoromethylthiocyproheptadine has been disclosed in British Pat. No. 1,336,335 but only as an intermediate in the synthesis of novel therapeutically useful compounds. There is no disclosed pharmacological activity for the compound itself and no suggestion that the compound exists as enantiomers or that the enantiomers would exhibit different pharmacological activities.

Surprisingly, it has now been found that levorotatory trifluoromethylthio derivatives of cyproheptadine are potent antipsychotic agents, and that both enantiomers thereof are platelet aggregation inhibitors useful as antithrombotic agents.

It is thus an object of the present invention to provide (−)- and (+)-trifluoromethylthiocyproheptadine derivatives as novel compounds with the aforementioned utilities.

It is a further object of this invention to provide novel processes for the preparation of the novel compounds.

Another object of the invention is to provide novel pharmaceutical compositions comprising the novel compounds or mixtures thereof as active ingredient.

Another object of the invention is to provide a novel method of treating psychoses by administration of the levorotatory or racemic compounds or pharmaceutical compositions thereof to a patient.

It is also an object of this invention to provide a novel method of treatment of thrombosis by administration of the novel compounds or mixtures thereof, or pharmaceutical compositions thereof to a patient.

DETAILED DESCRIPTION OF THE INVENTION

The novel compounds of this invention are the levorotatory and dextrorotatory enantiomers of the compound having the following structural formula:

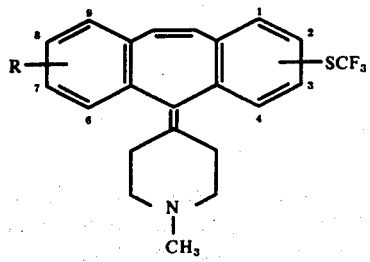

or pharmaceutically acceptable salt thereof, wherein R represents hydrogen, lower alkyl, especially $C_{1-3}$ alkyl, or fluoro.

A preferred embodiment of the novel compounds is that wherein R is hydrogen.

An even more preferred embodiment of the novel compounds is that wherein R is hydrogen, and the $-SCF_3$ group is in the 3-position.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, pamoate, citrate, napsylate, pyruvate, isethionate, maleate, furmarate, or the like.

The salts are prepared by dissolving equimolecular amounts of the free base compound and the desired acid in warm water followed by cooling to precipitate the salt product.

The introduction of nuclear substituents into aromatic rings of cyproheptadine derivatives and analogs results not only in significant changes in the biological spectra of these compounds, but also results in the introduction of optical isomerism. Optical isomerism due to restricted rotation is known as atropisomerism. The resulting enantiomers or optical isomers are also known as atropisomers. (Ebnother et al., *Helv. Chim. Acta*, 48, 1237–1249 (1965)). In the case of cyproheptadine derivatives and analogs that are unsymmetrically substituted, such as the 3-substituted analogs and derivatives, atropisomerism results from the non-bonded interactions between the aromatic protons in the 4- and 6-positions and the allylic protons of the piperidine ring. These non-bonded interactions restrict the inversion of the 7-membered ring in the cyproheptadine derivatives and analogs thus leading to atropisomerism. In the case of these cyproheptadine analogs and derivatives, the free energy barriers to inversion are sufficiently high to allow the isolation and characterization of the atropisomers.

An important novel process for preparing certain of the novel compounds of this invention comprises introduction of the trifluoromethylthio group by treating the corresponding iodo compound with an excess of trifluoromethylthiocopper formed from bis(trifluoromethylthio)mercury and copper powder in an inert organic solvent such as dimethylformamide, hexamethylphosphoramide, or the like at 50° to about 100° C. for 2 to about 12 hours. The upper limits of temperature and time as expressed are not critical, however, higher temperatures and longer times of reaction are not advisable if the starting material is enriched in one or the other optical isomers, inasmuch as high temperatures can cause racemization thus reducing the

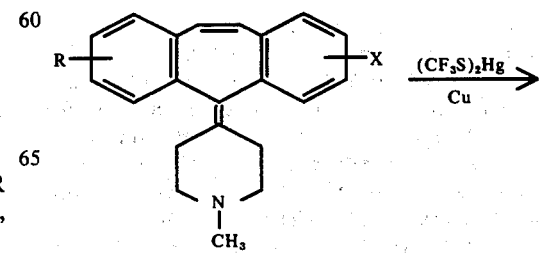

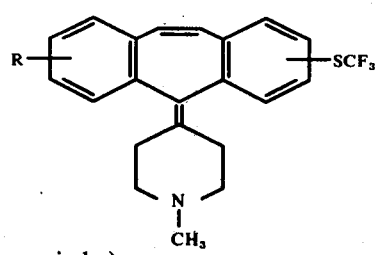

(wherein X is bromo or iodo.)
isomer purity of the product. If optical purity of the product is not important, temperatures as high as 200° C. and times as long as about 24 hours are not unreasonable.

In the foregoing description, the reagents are indicated to be bis-(trifluoromethylthio)mercury and copper. However, the reagent responsible for introduction of the trifluoromethylthio group in the novel process is in fact trifluoromethylthiocopper formed in situ from the above-named reagents.

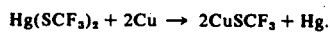

Another process useful for obtaining the optical isomers of the novel compounds of this invention comprises separation of the enantiomers of a novel starting material in their synthesis such as the iodo compounds from which the novel products can be obtained without loss of optical purity. This process comprises forming diastereomeric salts of a mixture of the desired optical isomers with one enantiomer of an optically active acid such as di-(p-toluoyl)tartaric acid, or malic acid, or the like, in a suitable solvent such as a lower alkanol, such as methanol, ethanol, propanol, or benzene, acetonitrile, nitromethane, acetone, or the like, and isolating by crystallization the less soluble diastereomeric salt. The isolated diastereomeric salt if desired may be then recrystallized until further recrystallization fails to change the degree of optical rotation. The desired optically active product as the free base is then obtained by treating the diastereomeric salt thereof with a base.

The other optical isomer is obtained from the mother liquors obtained above by crystallizing the salt therefrom, and if desired, repeated recrystallization to constant optical rotation, followed by liberation of the optically active free base.

Alternatively, the contents of the above described mother liquors are concentrated to dryness, the residue is treated with a base to liberate the optically impure free base. This is then treated with the optical antipode of the previously employed optically active acid to form the diastereomeric salt. If desired, this salt may be then purified by repeated recrystallization to constant optical rotation. The free base of the desired compound is then liberated from the diasteriomeric salt by treatment with a base.

Any of the optically enriched free base products or intermediates obtained as described above can be racemized by heating a solution of the product in an inert solvent until a sample fails to show optical activity. It is convenient to reflux a toluene solution for about 10-50 hours. In this manner, additional quantities of the racemic compounds can be obtained.

The starting materials required for practicing the novel processes of this invention are either known in the prior art or are readily obtained by the process outlined below. Details for the illustrated chemical transformations are provided in the Examples.

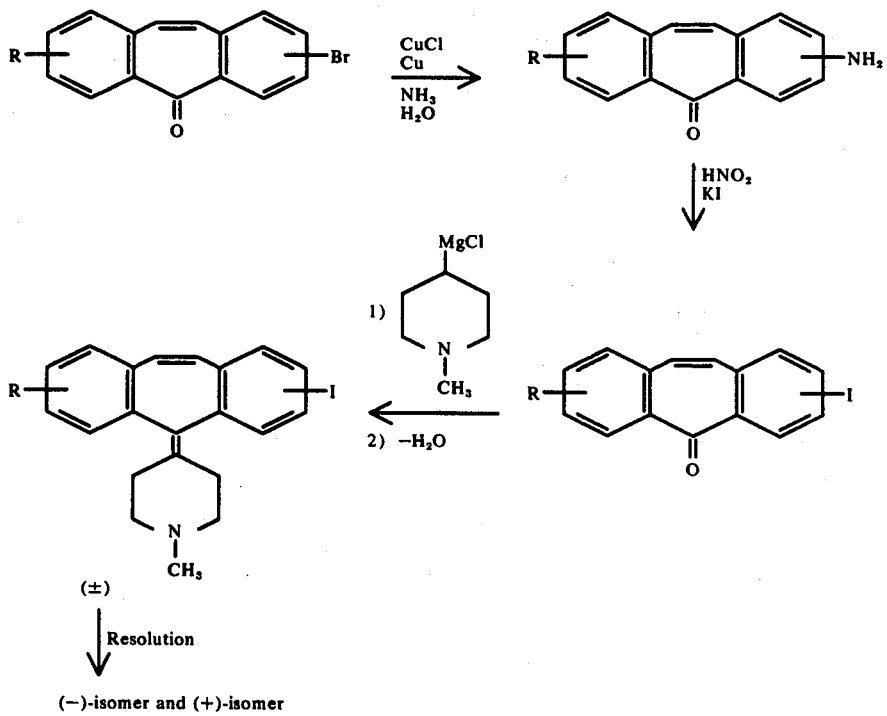

One novel method of treatment of this invention comprises the administration of one of the compounds, particularly a levorotatory enantiomer thereof to a psychotic patient. The route of administration can be oral, rectal, intravenous, intramuscular, or subcutaneous. Doses of 0.1 to 20 mg./kg./day and preferably of 0.5 to 10 mg./kg./day of active ingredient are generally adequate, and if preferred, it can be administered in divided doses given two to four times daily.

Another novel method of treatment of this invention comprises the administration of one of the compounds to a thrombotic patient. The route of administration can be oral, rectal, intravenous, intramuscular, or subcutaneous. Doses of 0.1 to 20 mg./kg./day and preferably of 0.5 to 5.0 mg./kg./day of active ingredient are generally adequate, and if prepared, it can be administered in divided doses given two to four times daily.

It is to be noted that the precise unit dosage form and dosage level depend upon the case history of the individual being treated and, consequently, are left to the discretion of the therapist.

Pharmaceutical compositions comprising a compound useful in the novel method of treatments as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleagninous solution or suspension. The amount of active ingredient incorporated in a unit dosage of the above described pharmaceutical compositions may be from 1 to 400 mg., and preferably from 5 to 250 mg.

EXAMPLE 1

(−)-1-methyl-4-(3-trifluoromethylthio-5H-dibenzo[a,d]-cyclohepten-5-ylidene)piperidine Step A:

Preparation of 3-amino-5H-dibenzo[a,d]cyclohepten-5-one

3-Bromo-5H-dibenzo[a,d]cyclohepten-5-one (25 g., 0.088 mole), copper turnings (1.14 g., 0.018 mole), cuprous chloride (0.94 g., 0.009 mole), and concentrated aqueous ammonia (50 ml.) are agitated together at 195° in a steel bomb for 24 hours.

The cooled mixture is removed from the vessel, and the large solid mass broken up mechanically and dissolved in warm chloroform (ca 150 ml.). The aqueous residue from the reaction is extracted once with chloroform, and the combined chloroform fractions are washed with water, dried over sodium sulfate, filtered, and evaporated in vacuo to give 18.9 g. of crude yellow solid.

The crude product is ground in a mortar and recrystallized from ethanol (ca 200 ml.). The solid obtained is dissolved in warm chloroform, treated with about 8 g. of silica gel, filtered, and evaporated in vacuo to give 16 g. of 3-amino-5H-dibenzo[a,d]cyclohepten-5-one.

Following the procedure of Step A, but substituting for the 3-bromo-5H-dibenzo[a,d]cyclohepten-5-one used therein an equimolar amount of 3-bromo-7-fluoro-5H-dibenzo[a,d]cyclohepten-5-one and 3-bromo-7-methyl-5H-dibenzo[a,d]cyclohepten-5-one, there are produced respectively 3-amino-7-fluoro-5H-dibenzo[a,d]cyclohepten-5-one and 3-amino-7-methyl-5H-dibenzo[a,d]cyclohepten-5-one.

Step B:

Preparation of 3-iodo-5H-dibenzo[a,d]cyclohepten-5-one

3-Amino-5H-dibenzo[a,d]cyclohepten-5-one (50 g., 0.226 mole) is slurried in 150 ml. of concentrated hydrochloric acid. Ice (150 ml.) is added, and the stirred mixture cooled in an ice bath and diazotized by dropwise addition of sodium nitrite solution (17 g., 0.248 mole in 80 ml. of water) over 45 minutes. The temperature is held below 5° throughout the addition. The mixture is stirred for an additional 15 minutes and poured slowly into a stirred solution of 160 g. (1 mole) of potassium iodide in 100 ml. of water. The mixture is stirred at room temperature for 1 hour, then stored overnight in the refrigerator.

The resulting slurry is filtered and the filtrate is extracted once with chloroform. The solids are extracted several times with hot chloroform, and the combined chloroform fractions washed with dilute sodium bisulfite and with water, and dried over sodium sulfate. Residual solid from the chloroform extraction is discarded.

The chloroform solution is combined with 100 g. of silica gel, evaporated in vacuo, then stirred with 1:1 chloroform/hexane and added to a column of 1 kg. of silica gel. The column is packed and eluted with 1:1 chloroform hexane. The product fraction, which is eluted after about 3.5 liters of fore-run, is evaporated in vacuo to give the 3-iodo-5H-dibenzo[a,d]cyclohept-ent-5-one (39.7 g., 53%) as a white solid, m.p. 97.5–99°.

Following the procedure of Step B but substituting for the 3-amino-5H-dibenzo[a,d]cyclohepten-5-one used therein an equimolecular amount of 3-amino-7-fluoro-5H-dibenzo[a,d]cyclohepten-5-one and 3-amino-7-methyl-5H-dibenzo[a,d]cyclohepten-5-one, there are produced respectively, 3-iodo-7-fluoro-5H-dibenzo[a,d]cyclohepten-5-one and 3-iodo-7-methyl-5H-dibenzo[a,d]cyclohepten-5-one.

Step C:

Preparation of (±)-1-methyl-4-(3-iodo-5H-dibenzo[a,d]cyclohepten-5-ylidene)piperidine To an ice-cooled solution of 10.00 g. (0.0301 mol) of 3-iodo-5H-dibenzo[a,d]cyclohepten-5-one in 100 ml. of dry tetrahydrofuran is added dropwise 64 ml. of 0.47M 1-methyl-4-piperidylmagnesium chloride in tetrahydrofuran. The solution is stirred one hour at room temperature, and then the tetrahydrofuran is removed on a rotary evaporator. The red-oily residue that remains is dissolved in benzene and water is added dropwise until a clear benzene supernatant and a gelatinous aqueous phase is obtained. The benzene phase is decanted and the gelatinous aqueous phase is extracted with two 100 ml. portions of hot benzene. The combined benzene extracts are concentrated. The residue that remains is triturated with acetonitrile, and the crystalline product is collected by filtration, washed with cold acetonitrile and dried to give 5.95 gm. (46%) of 1-methyl-4-(3-iodo-5-hydroxy-5H-dibenzo[a,d]cyclohepten-5-yl)piperidine.

A solution of 3.23 g. of 1-methyl-4-(3-iodo-5-hydroxy-5H-dibenzo[a,d]cyclohepten-5-yl)piperidine, 30 ml. of trifluoroacetic acid and 10 ml. of trifluoroacetic anhydride is refluxed for 6 hours. The solution is concentrated on a rotary evaporator and the residue is made basic with 5% sodium hydroxide solution. The oil that precipitates is extracted into ether, and this ether phase is washed with water, dried over magnesium sulfate, filtered, and the ether removed on a rotary evaporator. The residue is triturated with acetonitrile, collected and dried to give 2.36 g. of material. This material is recrystallized from ethyl acetate to give pure (±)-1-methyl-4-(3-iodo-5H-dibenzo[a,d]cyclohepten-5-ylidene)piperidine, m.p. 166°–170°.

Anal. Calcd. for $C_{21}H_{20}IN$: C, 61.03; H, 4.88; N, 3.38, I, 30.70. Found: C, 61.35; H, 5.01; N, 3.30, I, 30.62.

Following the procedure substantially as described in Example 1, Step C, but substituting for the 3-iodo-5H-dibenzo[a,d]cyclohepten-5-one used therein, an equimolar amount of 7-fluoro-3-iodo-5H-dibenzo[a,d]cyclohepten-5-one and 3-iodo-7-methyl-5H-dibenzo[a,d]cyclohepten-5-one, there are produced respectively (±)-1-methyl-4-(7-fluoro-3-iodo-5H-dibenzo[a,d]cyclohepten-5-ylidene)piperidine and (±)-1-methyl-4-(3-iodo-7-methyl-5H-dibenzo[a,d]cyclohepten-5-ylidene)piperidine.

Step D:

Resolution of (±)-1-methyl-4-(3-iodo-5H-dibenzo[a,d]cyclohepten-5-ylidene)piperidine A. Levorotatory Isomer - To a solution of 4.60 g. (0.0111 mol) of (±)-1-methyl-4-(3-iodo-5H-dibenzo[a,d]cyclohepten-5-ylidene)piperidine in 100 ml. of hot absolute ethanol is added 4.30 g. (0.0111 mol) of di-p-toluoyl-d-tartaric acid dissolved in 45 ml. of warm absolute ethanol. The solution is stirred and allowed to cool to room temperature. The crystalline precipitate that forms is removed by filtration, washed with cold absolute ethanol, and dried at 100° in vacuo to give 2.36 g. of material designated A. The clear ethanol filtrate and washings, which are combined and concentrated by boiling to 50 ml., are designated B.

The 2.36 g. of A is recrystallized from absolute ethanol four times to give a product that has a constant rotation, m.p. 156°–157°; $[\alpha]_{589}^{25} = -129°$, $[\alpha]_{578}^{25} = -136°$, $[\alpha]_{546}^{25} = -126°$ (c $[\alpha]_{436}^{25} = -371°$ (c = 0.00407 g./ml. pyridine). This material, 0.35 g. is suspended in a small amount of water and is treated with sodium hydroxide solution. The free base that precipitates is extracted into ether, washed with water, and dried over magnesium sulfate. After filtering, the ether is removed on a rotary evaporator. The white solid that remains is recrystallized from acetonitrile to give 0.12 g. of (−)-1-methyl-4-(3-iodo-5H-dibenzo[a,d]cyclohepten-5-ylidene)piperidine, m.p. 184°–190°; $[\alpha]_{589}^{25} = -141°$, $[\alpha]_{578}^{25} = -149°$, $[\alpha]_{546}^{25} = -180°$, $[\alpha]_{436}^{25} = -437°$ (c = 0.00356 g./10 ml. $CHCl_3$).

Anal. Calcd. for $C_{21}H_{20}IN$: C, 61.03; H, 4.88; N, 3.38; I, 30.70. Found: C, 60.66; H, 5.25; N, 3.28; I, 30.83.

B. Dextrorotatory Isomer - The ethanol filtrate and washings, designated B, are concentrated on a rotary evaporator. The residue is treated with sodium carbonate solution. The free base that precipitates is extracted into ether. Evaporation of the ether gives 2.23 g. of a solid that is dissolved in 75 ml. of hot absolute ethanol and treated with 2.18 g. of di-p-toluoyl-l-tartaric acid monohydrate in 20 ml. of hot absolute ethanol. The solution is stirred and concentrated by boiling to 45 ml. The crystalline precipitate that forms on cooling is removed by filtration, washed with cold absolute ethanol, and dried at 100° in vacuo to give 2.00 g. of material. This material is recrystallized from absolute ethanol to give a product that has a constant rotation, m.p. 155°–157°; $[\alpha]_{589}^{25} = +128°$, $[\alpha]_{578}^{25} = +136°$, $[\alpha]_{546}^{25} +162°$, $[\alpha]_{436}^{25} = +372°$, (c =0.00181 g./ml pyridine). This material, 0.53 g., is suspended in a small amount of water and is treated with sodium hydroxide solution. The free base that precipitates is extracted into ether, washed with water, and dried over magnesium sulfate. After filtering, the ether is removed on a rotary evaporator. The residue is triturated with acetonitrile, collected by filtration, and dried to give 0.18 g. of (+)-1-methyl-4-(3-iodo-5H-dibenzo[a,d]cyclohepten-5-ylidene)piperidine, m.p. 188°–191°; $[\alpha]_{589}^{25} = +139°$, $[\alpha]_{578}^{25} = +145°$, $[\alpha]_{546}^{25} = +175°$, $[\alpha]_{436}^{25} = +430°$, (c = 0.00137 g./ml. $CHCl_3$).

Anal. Calcd. for $C_{21}H_{20}IN$: C, 61.03; H, 4.88; N, 3.38 Found: C, 61.27; H, 5.21; N, 3.20.

Employing the procedure substantially as described in Example 1, Step D, but substituting for the (±)-1-methyl-4-(3-iodo-5H-dibenzo[a,d]cyclohepten-5-ylidene)piperidine used therein, an equimolar amount of (±)-1-1-methyl-4-(7-fluoro-3-iodo-5H-dibenzo[a,d]cyclohepten-5-ylidene)piperidine and (±)-1-methyl-4-(3-iodo-7-methyl-5H-dibenzo[a,d]cyclohepten-5-ylidene)piperidine, there is produced respectively the levo- and dextrorotatory isomers thereof.

Step E:

Preparation of (−)-1-methyl-4-(3-trifluoromethylthio-5-H-dibenzo[a,d]cyclohepten-5-ylidene)piperidine A mixture of 1.42 g. (0.0024 mol) of copper dust, 2.47 g. (0.00615 mol) of bis-(trifluoromethylthio)mercury, 1.27 g. (0.00307 mol) of (−)-1-methyl-4-(3-iodo-5H-dibenzo[a,d]cyclohepten-5-ylidene)piperidine and 15 ml. of dimethylformamide is stirred and heated on the steam bath for four hours. The mixture is cooled in ice and 25 ml. of chloroform and 25 ml. of concentrated ammonium hydroxide is added. The mixture is stirred overnight at room temperature and then filtered through a pad of Filter-Cel. The filtrate and chloroform washings are combined and separated from the deep blue aqueous phase. The chloroform phase is washed with water, dried over magnesium sulfate, filtered, and the chloroform is removed on a rotary evaporator. The residue crystallizes rapidly. It is triturated with cold acetonitrile and collected by filtration. This material is recrystallized from acetonitrile to give 0.40 g. (34%) of (−)-1-methyl-4-(3-trifluoromethylthio-5H-dibenzo[a,d]cyclohepten-5-ylidene) piperidine, m.p. 130°–132°; $[\alpha]_{589}^{25} = -58.4°$, $[\alpha]_{578}^{25} = -62.4°$, $[\alpha]_{546}^{25} = -76.9°$, $[\alpha]_{436}^{25} -206°$, (c = 0.00498 g./ml. $CHCl_3$).

Anal. Calcd. for $C_{22}H_{20}F_3NS$: C, 68.19; H, 5.20; N, 3.62; F, 14.71. Found: C, 68.67; H, 5.54; N, 3.37; F, 14.50.

Employing the procedure substantially as described in Example 1, Step E, but substituting for the (−)-1-methyl-4-(3-iodo-5H-dibenzo[a,d]cyclohepten-5-ylidene)piperidine used therein an equimolar amount of (−)-1-methyl-4-(7-fluoro-3-iodo-5H-dibenzo[a,d]cyclohepten-5-ylidene)piperidine and (−)-1-methyl-4-(3-iodo-7-methyl-5H-dibenzo[a,d]cyclohepten-5-ylidene)piperidine, there is produced respectively (−)-1-methyl-4-(7-fluoro-3-trifluoromethylthio-5H-dibenzo[a,d]cyclohepten-5-ylidene)piperidine and (−)-1-methyl-4-(7-methyl-3-trifluoromethylthio-5H-dibenzo[a,d]cyclohepten-5-ylidene)piperidine.

EXAMPLE 2

(+)-1-Methyl-4-(3-trifluoromethylthio-5H-dibenzo[a,d]cyclohepten-5-ylidene)piperidine A mixture of 2.24 g. (0.0353 mol) of copper dust, 3.90 g. (0.0097 mol) of bis-(trifluoromethylthio)mercury, 2.00 g. (0.00484 mol) of (+)-1-methyl-4-(3-iodo-5H-dibenzo[a,d]cyclohepten-5-ylidene)piperidine and 20 ml. of dimethylformamide is stirred and heated on the steam bath for six hours. The mixture is cooled in an ice bath and 100 ml. of chloroform and, 30 ml. of concentrated ammonium hydroxide is added. The mixture is stirred overnight at room temperature and is filtered through a pad of Filter-Cel. The filtrate and chloroform washings are combined and separated from the deep blue aqueous phase. The chloroform phase is washed with water, dried over magnesium sulfate, filtered, and the chloroform is removed on a rotary evaporator. The residue crystallizes rapidly. It is triturated with cold acetonitrile and collected by filtration. This material is recrystallized from acetonitrile to give 0.45 g. (39%) of (+)-1-methyl-4-(3-trifluoromethylthio-5H-dibenzo[a,d]cyclohepten-5-ylidene)piperidine, m.p. 130°–132°; $[\alpha]_{589}^{25} = +58.7°$, $[\alpha]_{578}^{25} = +63.0°$, $[\alpha]_{546}^{25} = +76.8°$, $[\alpha]_{436}^{25} = +204°$ (c = 0.0079 gm./ml. CHCl$_3$).

Anal. Calcd. for $C_{22}H_{20}F_3NS$: C, 68.19; H, 5.20; N, 3.62; F, 14.71. Found: C, 68.42; H, 5.27; N, 3.35; F, 14.47.

Employing the procedure substantially as described in Example 2, but substituting for the (+)-1-methyl-4-(3-iodo-5H-dibenzo[a,d]cyclohepten-5-ylidene)piperidine used therein an equimolar amount of (+)-1-methyl-4-(7-fluoro-3-iodo-5H-dibenzo[a,d]cyclohepten-5-ylidene)piperidine and (+)-1-methyl-4-(3-iodo-7-methyl-5H-dibenzo[a,d]cyclohepten-5-ylidene)piperidine, there is produced respectively (+)-1-methyl-4-(7-fluoro-3-trifluoromethylthio-5H-dibenzo[a,d]cyclohepten-5-ylidene)piperidine and (+)-1-methyl-4-(7-methyl-3-trifluoromethylthio-5H-dibenzo[a,d]cyclohepten-5-ylidene)piperidine.

EXAMPLE 3

(±)-1-Methyl-4-(3-trifluoromethylthio-5H-dibenzo[a,d]cyclohepten-5-ylidene)piperidine Step A:

Preparation of 3-trifluoromethylthio-5H-dibenzo[a,d]cyclohepten-5-one

A mixture of 17.57 g. (0.0062 mol) of 3-bromo-5H-dibenzo[a,d]cyclohepten-5-one, 42.56 g. (0.1056 mol) of bis-(trifluoromethylthio)mercury, 28.0 g. (0.44 mol) of copper powder (Electrolytic dust), 98 ml. of quinoline and 8.4 ml. of pyridine is stirred and heated at 195° for 18 hours. The cooled, dark reaction mixture is diluted with 200 ml. of benzene and 400 ml. of 6N hydrochloride acid, stirred vigorously, and filtered through a pad of Filter-Cel. The aqueous acid phase is removed and extracted with 100 ml. of ether. The ether phases are combined and are washed with five 300 ml. of portions of 3N hydrochloric acid, five 300 ml. portions of water, and dried over magnesium sulfate. After filtering, the benzene is removed by filtration. The residue, which crystallizes readily, is recrystallized from methanol to give 14.83 g. (78%) of 3-trifluoromethylthio-5H-dibenzo[a,d]cyclohepten-5-one, m.p. 87°–88°, that is 98% pure by glc.

Step B:

Preparation of (±)-1-methyl-4-(3-trifluoromethylthio-5H-dibenzo[a,d]cyclohepten-5-ylidene)piperidine To an ice cooled solution of 5.00 (0.0613 mol) of 3-trifluoromethylthio-5H-dibenzo[a,d]cyclohepten-5-one in 80 ml. of dry tetrahydrofuran is added dropwise 50 ml. of 0.35N 1-methyl-4-piperidylmagnesium chloride in tetrahydrofuran. The solution is stirred for 1 hour, and then the tetrahydrofuran is removed on a rotary evaporator. The red-oily residue that remains is dissolved in benzene and water is added dropwise until a clear benzene supernatent and a gelatinous aqueous phase is obtained. The benzene phase is decanted and the gelatinous aqueous phase is extracted with three 50 ml. portions of hot benzene. The combined benzene phases are washed with water and the benzene is removed on a rotary evaporator. The residue is triturated with cold acetonitrile and collected by filtration to give 2.81 g. of 1-methyl-4-(3-trifluoromethylthio-5-hydroxy-5H-dibenzo[a,d]cyclohepten-5-yl)piperidine.

A solution of 2.81 g. of 1-methyl-4-(3-trifluoromethylthio-5-hydroxy-5H-dibenzo[a,d]cyclohepten-5-yl)piperidine in 50 ml. of 6N hydrochloric acid and 10 ml. of n-butanol is stirred and refluxed for 21 hours. The bulk of the solvents is removed by evaporation on a rotary evaporator. The residue is made basic with 5% sodium hydroxide solution and the oil that precipitates is extracted into chloroform. The chloroform phase is washed with water, dried over magnesium sulfate, filtered, and the chloroform removed on a rotary evaporator. The material is recrystallized from the acetonitrile to give 1.90 g. of (±)-1-methyl-4-(3-trifluoromethylthio-5H-dibenzo[a,d]cyclohepten-5-ylidene)piperidine, m.p. 115°–116.5°.

Anal. Calcd. for $C_{22}H_{20}F_3NS$: C, 68.19; H, 5.20; N, 3.62; F, 14.71; S, 8.28. Found: C, 68.37; H, 5.30; N, 3.50, F, 14.48; S, 8.35.

Employing the procedure substantially as described in Example 3 but substituting for the 3-bromo-5H-dibenzo[a,d]cyclohepten-5-one used in Step A thereof, an equimolar amount of 3-bromo-7-fluoro-5H-dibenzo[a,d]cyclohepten-5-one, and 3-bromo-7-methyl-5H-dibenzo[a,d]cyclohepten-5-one, there are produced respectively (±)-1-methyl-4-(3-trifluoromethylthio-7-fluoro-5H-dibenzo[a,d]cyclohepten-5-ylidene)piperidine and (±)-1-methyl-4-(3-trifluoromethylthio-7-methyl-5H-dibenzo[a,d]cyclohepten-5-ylidene)piperidine.

EXAMPLE 4

Pharmaceutical Compositions

A typical tablet containing 100 mg. of (−)-1-methyl-4-(3-trifluoromethylthio-5H-dibenzo[a,d]cyclohepten-5-ylidene)piperidine per tablet is prepared by mixing together with the active ingredient calcium phosphate, lactose and starch in the amounts shown in the table below. After these ingredients are thoroughly mixed, the appropriate amount of magnesium stearate is added and the dry mixture is then compressed into tablets.

Tablet Formula

| Ingredient | Mg. per Tablet |
|---|---|
| (-)-1-methyl-4-(3-trifluoro-methylthio-5H-dibenzo[a,d]-cyclohepten-5-ylidene)piperidine | 100 mg. |
| Calcium phosphate | 52 mg. |
| Lactose | 60 mg. |
| Starch | 10 mg. |
| Magnesium stearate | 1 mg. |

What is claimed is:

1. A levorotatory or dextrorotatory enantiomer of a compound of structural formula:

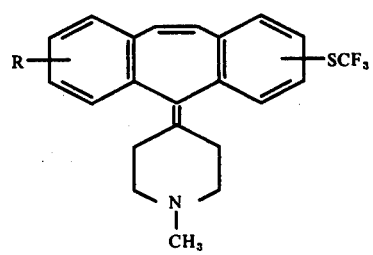

or pharmaceutically acceptable salt thereof, wherein R is hydrogen, fluoro or lower alkyl.

2. The compound of claim 1 which the levoroatory enantiomer of 1-methyl-4-(3-trifluoromethylthio-5H-dibenzo[a,d]cyclohepten-5-ylidene)piperidine or pharmaceutically acceptable salt thereof.

3. The compound of claim 1, which is the dextrorotatory enantiomer of 1-methyl-4-(3-trifluoromethylthio-5H-dibenzo[a,d]cyclohepten-5-ylidene)piperidine or pharmaceutically acceptable salt thereof.

4. A method of treating psychoses which comprises the administration to a patient in need of such treatment an effective amount of a compound of formula:

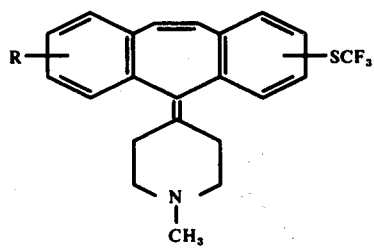

or pharmaceutically acceptable salt thereof wherein R is hydrogen, fluoro, or lower alkyl.

5. The method of claim 4 wherein the compound is the levorotatory enantiomer of 1-methyl-4-(3-trifluoromethylthio-5H-dibenzo[a,d]cyclohepten-5-ylidene)piperidine or pharmaceutically acceptable salt thereof.

6. A method of treating thrombosis which comprises the administration, to a patient in need of such treatment, an effective amount of a compound of formula:

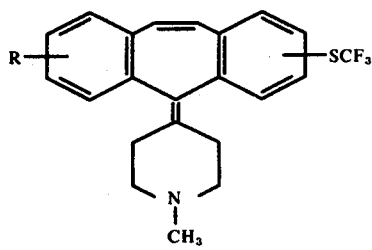

or pharmaceutically acceptable salt thereof, wherein R is hydrogen, fluoro, or lower alkyl.

7. The method of claim 6, wherein the compound is 1-methyl-4-(3-trifluoromethylthio-5H-dibenzo[a,d]cyclohepten-5-ylidene)piperidine or pharmaceutically acceptable salt thereof.

8. A pharmaceutical composition in unit dosage form comprising a pharmaceutical carrier and an effective amount of one enantiomer of a compound of formula:

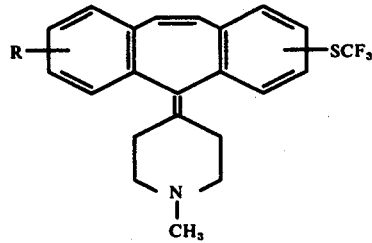

or pharmaceutically acceptable salt thereof, wherein R is hydrogen, fluoro, or lower alkyl.

9. The pharmaceutical composition of claim 8, wherein the compound is one enantiomer of 1-methyl-4-(3-trifluoromethylthio-5H-dibenzo[a,d]cyclohepten-5-ylidene)piperidine or pharmaceutically acceptable salt thereof.

* * * * *